United States Patent
Macher et al.

[11] Patent Number: 6,066,164
[45] Date of Patent: May 23, 2000

[54] HEATING DEVICE FOR HEATING A SKIN SURFACE ON PARTIAL AREAS OF THE HUMAN BODY

[76] Inventors: David Macher, Maigasse 8, 8-8570 Voitsberg; Heinz Zorn, Höf 285, A-8063 Eggersdorf, both of Austria

[21] Appl. No.: 09/034,715

[22] Filed: Mar. 4, 1998

[30] Foreign Application Priority Data

May 6, 1997 [AT] Austria ..................... 770/97

[51] Int. Cl.[7] .................................................. A61F 7/00
[52] U.S. Cl. .................. 607/96; 607/152; 607/149; 607/72; 219/528; 219/549
[58] Field of Search ................. 607/96, 98, 99, 607/115, 152, 154, 155, 156, 149, 72; 604/20; 219/211, 527, 528, 549, 546

[56] References Cited

U.S. PATENT DOCUMENTS

| | | | |
|---|---|---|---|
| 4,042,803 | 8/1977 | Bickford | 219/211 |
| 4,279,255 | 7/1981 | Hoffman | 128/402 |
| 4,381,009 | 4/1983 | Bon | 607/96 |
| 4,922,906 | 5/1990 | Takeuchi et al. | 607/72 |
| 5,140,131 | 8/1992 | Macher et al. | |
| 5,531,775 | 7/1996 | Sasaki et al. | 607/96 |
| 5,601,618 | 2/1997 | James | 607/71 |

FOREIGN PATENT DOCUMENTS

| | | |
|---|---|---|
| 0552482 A2 | 7/1993 | European Pat. Off. |
| 3602572 A1 | 8/1986 | Germany . |

*Primary Examiner*—Linda C. M. Dvorak
*Assistant Examiner*—R Kearney
*Attorney, Agent, or Firm*—Alston & Bird LLP

[57] ABSTRACT

The invention relates to a heating device (1), particularly for heating and/or maintaining the temperature of a skin surface with a depth effect on partial areas of a human body. The latter has at least one heat transfer element (2) comprising a heating element (3) and an energy supply device connected by an energy transfer device to the heat transfer element (2), and preferably a control and/or switching device (9). In order to supply the heating element (3) with energy, an oscillating switch circuit is located in the control and/or switching device (9) in order to generate constant pulse signals. Following this is an adjustable pulse modulation switching circuit for altering the pulse signals for controlling a power end stage.

26 Claims, 4 Drawing Sheets

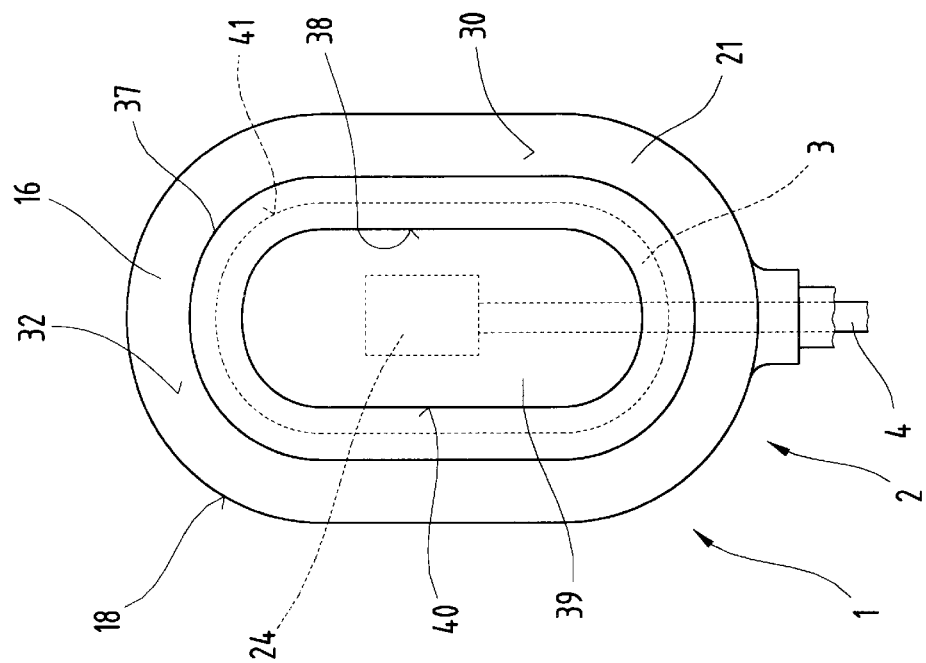
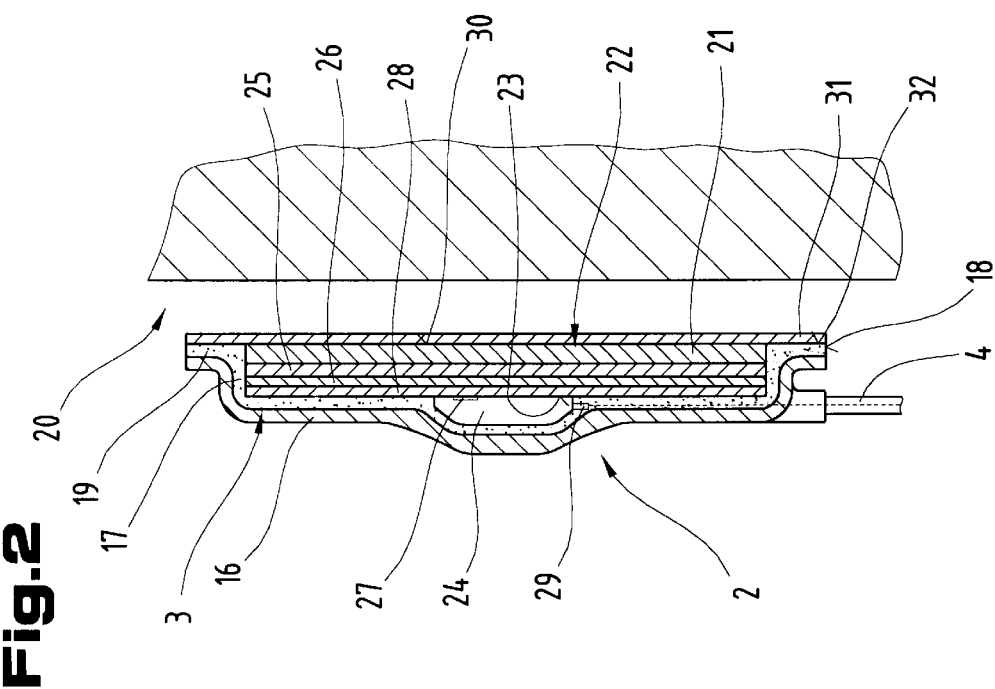

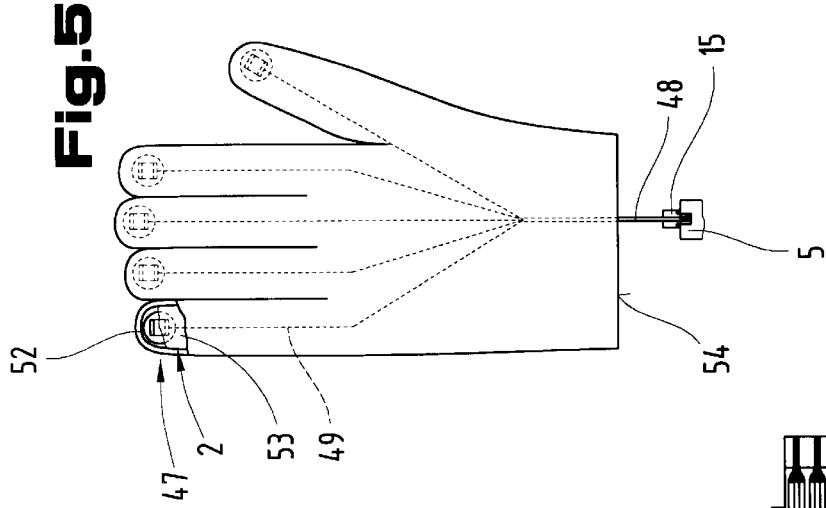
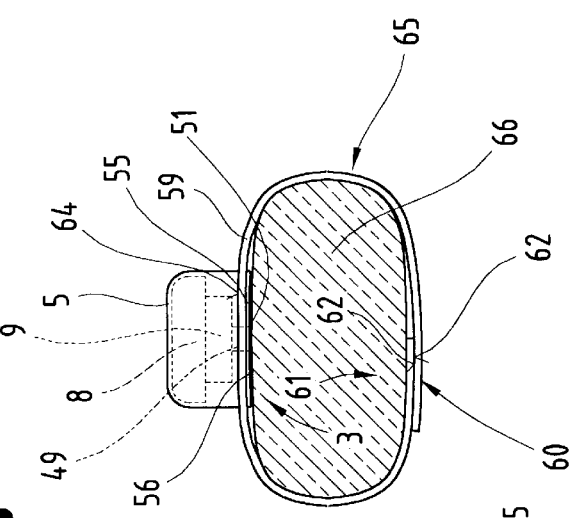
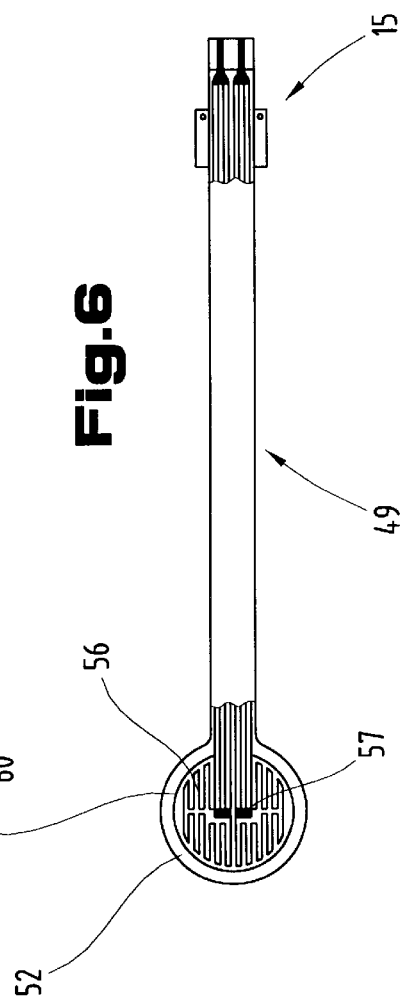

HEATING DEVICE FOR HEATING A SKIN SURFACE ON PARTIAL AREAS OF THE HUMAN BODY

BACKGROUND OF THE INVENTION

1. Field of the Invention

The invention relates to a heating device as described in the preamble to claim 1.

2. The Prior Art

A heating device is already known According to U.S. Pat. No. 4,279,255 A, which comprises a heating device by means of which heat is applied to a localised area of a body. In this case the heating device consists of a flexible heating unit, containing a plurality of electrical resistive heating elements which are supplied with electrical power by means of a battery inserted in a battery pack. For this purpose the battery is connected to the resistive heating element via an energy transfer device, particularly electrically conductive wires, the length of which is of such dimensions that the heating device can be located on body parts which are remote from the centre of gravity of the body. The battery pack with the inserted battery lies roughly at the centre of gravity of the body. Moreover, a switch member in the form of a selector switch is secured with the power supply device at the battery pack, and by means of which each resistive heating element can be switched on and off, so that the quantity of heat energy can be adapted to varying requirements. Furthermore the heating device has attachment means in order to locate the battery pack roughly at the centre of gravity of the body, and further attachment means by means of which the heating device can be located on a body part.

A disadvantage in this construction is that for long-term operation correspondingly large batteries are necessary due to a high energy requirement, and maintenance of a predetermined temperature is only possible within relatively large boundaries, so that the comfort of wearing the heating device is considerably reduced and in particular mobile use is rendered difficult.

SUMMARY OF THE INVENTION

The object of the invention is to provide a heating device which may be regulated in its effect, and which is characterised by economic utilisation of energy.

The purpose of the invention is achieved in order to supply the heating element with energy there is located in the control and/or switching device an oscillating switching circuit for generating constant pulse signals, and following said oscillator switching circuit is an adjustable pulse modulation switching circuit for altering the pulse signals for controlling the power end stage for energy supply to the heating element from the energy source. The surprising advantage in this respect is that the application of energy by the pulsed action on the heating element and the efficient energy utilisation achieved thereby with simultaneous sensitive regulation to the temperature necessary for the treatment of a body part is achieved at small capacities of energy sources and over a long period of time.

A design of the heating device is advantageous so that the power end stage is formed by at least one switch member, such for example as a transistor FET, etc. Further in this respect it is possible, as in this way simple control of the final power stage is achieved for supplying the heating element with energy.

Also it is advantageous that the power end stage is located in the supply apparatus. An advantage is this respect is that by means of which an extremely compact supply apparatus and in connection with this an extremely thin, easy-to-carry heat transfer element is achieved.

It is also possible that the power end stage is located in the heat transfer element. So in this way simultaneously a spot heating source is achieved in the area of the heat transfer element.

In other embodiments it is possible that the pulse modulation switching circuit is conductively connected to a temperature selector regulator for temperature regulation of the heating element. So it is advantageous that a sensitive staged or infinitely variable temperature regulation is achieved for the heating element.

In other embodiments the heating device can be located in a simple way at the most varied areas of a body, and may be used several times for treatments, close body contact being achieved in each cases. So it is possible that the heat transfer element is preferably releasably located via an adhesive layer on the partial area of the body or on a body zone, particularly on the skin surface.

In a further embodiment the heat transfer element is of a layered construction, and has at least one base layer, with an inner side facing the body zone, upon which is located at least one heating element. So it is more advantageous that the heat loss due to radiation into the environment is reduced.

Further it is possible that the heating element (3) is formed by a surface heating element, particularly a heating conductive layer and if necessary a semiconductor component, e.g. a switch member, e.g. transistor, FET, etc. forming a spot heat source. So a high regularity of heat effect during long-term therapy is achieved with small temperature tolerances.

A further advantage of the heating device is that a cover layer is located on a heat transfer surface of the heating element facing the body zone and facing away from the inner side. This embodiment of the heating device is advantageous because direct skin contacts of the heating element and thus ensuring skin irritations are avoided.

A further advantageous embodiment of the heating device is that the adhesive layer is preferably non-releasably located on a support surface of the base layer facing the body zone, and/or the base surface of the cover layer facing the body zone, preferably non-releasably. This design has the advantage that when the heating device is removed from the body, the adhesive layer on the heating device remains and thus it is possible to use the heating device several times for heating points of the body.

A further development of the heating device has the advantage that an adhesive surface has a configuration annularly surrounding the cover layer. This development is advantageous because a securely-adhering connection is provided and thus involuntary loosening of the heating device from the body is avoided, and further heat losses in the connection area between the heating device and the body are avoided.

A further advantage is that the base layer forms a recess, in which the heating element is located, or the heating element and the cover layer are located therein. So a receiving means is provided for the heating element and simultaneous application of the adhesive layer and of the heating element or of the cover layer on the body is achieved.

A further advantageous construction is that the heating element is formed from a plastic film, particularly a glassfibre-reinforced epoxy resin film, from a heating conductive layer and if necessary a corrosion protective layer of varnish, e.g. a protective varnish layer. So the layered construction of the heating element is advantageous because it is easy to produce, and which because of this has a structure which is protected against external influences, and is e.g. corrosion-proof.

Further of advantage is that the heating conductive layer is formed for example of rolled copper or silver or oxides thereof. So it is possible that a heating conductor layer is formed which is highly conductive and thus causes little energy loss.

In further embodiments of this heating device it is advantageous that the cover layer is formed from resilient non-woven material with a hypoallergenic adhesive, and is microporous and breathable. So it is possible that the action or the occurrence of secretions in the partial area of the body, particularly of the skin, and skin irritations are avoided.

In a further construction of the heating device it is advantageous that the heat transfer element, particularly for protection from contamination during transport and storage, is provided on the contact surface having the adhesive surface with a detachable plastic film. So it is advantageous that a contamination of the heating device, particularly of the adhesive layer, for example during transport, is avoided.

In a further embodiment the base layer has an aperture which surrounds the energy transfer device, particularly a cable. And in an advantageous construction the cable has a plug for detachable connection to the supply apparatus. By means of the further development the convenience of wearing and using the heating device is further increased.

A further embodiment is that the cover layer has a recess for receiving a non-woven material projecting over the base surface in the opposite direction to the body zone. So it is possible that an air cushion is provided which contributes to pleasant and uniform heating of a partial area of a body.

It is also advantageous that the non-woven material serves to accommodate a liquid active ingredient. In a favourable further development the "dry" heat therapy is reinforced by the use of additional therapeutic means, and an additional positive medical effect is achieved.

In an other embodiment it is possible that a portable supply apparatus provided with chargeable accumulators, is conductively connected to the heating element for energy supply thereof. Also of advantage is a further as in this way the heat therapy may be used without hindering the mobility of the user.

In other advantageous embodiments the control and switching device is located in the supply apparatus. Also of advantage is a design by means of which the therapeutic device to be worn on the body part to be treated has no components preventing wearing, and the devices necessary for power supply, inclusive of control and regulating elements, are integrated in the portable supply apparatus, e.g. on a belt, support sling, etc.

It is advantageous that a plurality of heat transfer elements are connected to a supply apparatus via a supply cable. A design like this is also possible, by means of which, proceeding from a supply apparatus, simultaneously a plurality of body parts to be treated can be supplied with heat.

In other embodiments at least one heat transfer element is located in a glove, particularly between an envelope and an inner liner. Further it is advantageous that at least one heat transfer element is located in a shoe, particularly an inner shoe. Advantageous further enable use of the heating device if necessary in the short term to protect particularly exposed body points from excessive chilling.

Finally an other embodiment of the heat transfer element is located on a flexible carrier strip, and the carrier strip forms a receiving means for the supply apparatus. It is also advantageous that the carrier strip is provided in end areas with a Velcro closure. And it is advantageous that the heating device is used directly by looping around a body part, and thus an extremely direct contact is achieved, by means of which economic utilisation of energy can be achieved and controlled use in the case of specific illnesses.

BRIEF DESCRIPTION OF THE DRAWINGS

The invention will be explained in more detail in the following with reference to the embodiments given by way of example and shown in the Figures.

Shown are:

FIG. 2: a heat transfer element of the heating device according to the invention in cross-section along lines II—II in FIG. 1;

FIG. 3: a further construction of the heat transfer element in cross-section;

FIG. 5: a further design of the heating device according to the invention with a plurality of heating elements in a garment;

FIG. 6: a further design of a heat transfer element of the heating device according to the invention in elevation, in partial section;

FIG. 7: a design of the heating device according to the invention for looping around a body part.

DETAILED DESCRIPTION OF PREFERRED EMBODIMENTS

It should firstly be noted that in the case of the various embodiments described, identical parts have been provided with identical reference numbers or identical components titles, the disclosures contained in the entire description being capable of transfer to identical parts with identical reference numbers or identical component titles. Furthermore, individual features from the various embodiments shown can in themselves represent independent solutions according to the invention.

Figure 1:
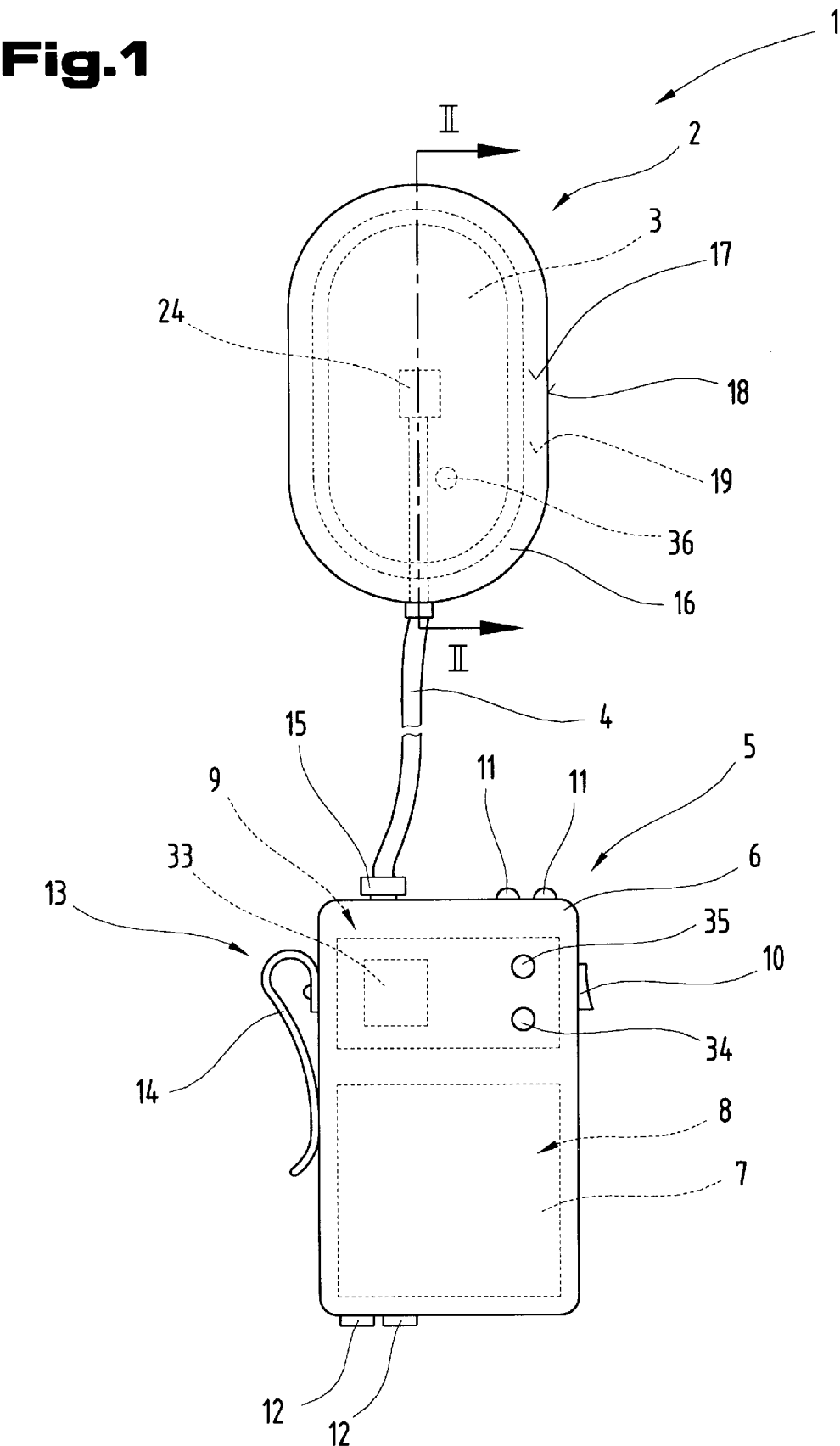
FIG. 1: the heating device according to the invention in a schematic view.

FIG. 1 shows a heating device 1 for neat therapy. The use of such a heating device 1 is suitable wherever a pain-relieving, relaxing or similarly pleasant effect is required on the human body or on body parts by means of heat. Examples of this are rheumatic complaints, muscle tension, back complaints, chills of the jawbone and sinuses, bladder, kidneys, menstrual complaints, nerve pain, whiplash syndrome or reinforcement of the absorption of remedies which are applied to body parts in the form of lotions. The heating device 1 may also be feasibly used for keeping warm or heating up exposed body parts, such e.g. as hands, feet, etc., and it is possible for such a case of application to locate the heating device 1 in a suitable way in gloves, shoes or other garments.

The heating device 1 has a flat, e.g. circular or ellipsoid heat transfer element 2, which is of a multi-layer construction and comprises substantially at least one heating element 3, which is connected via a cable 4 to a portable supply apparatus 5. The supply apparatus 5 consists of a housing 6, in which an energy source 8 is located which is exchangeable, for example by means of accumulators 7. Further located in the housing 6 is a control and/or switch device 9, via which the heating element 3 can be supplied with power from the accumulators 7 in a regulated manner. For operation of the heating device 1, the supply apparatus 5 has an on-and-off switch 10, monitoring lamps 11 and if necessary connector sockets 12 for recharging the accumulators 7 via an external charging device. Furthermore the supply device 5 may be equipped with an attachment device 13, e.g. a so-called belt clip 14. The cable 4 may be connected to the supply apparatus 5, as shown in the embodiment, via a releasable plug 15.

One possible embodiment of the layered construction of the heat transfer element 2 is shown in FIG. 2. A circular or ellipsoid, film-like base layer 16, consisting for example of a resilient aid heat-insulating breathable material, is coated on one side with a hypoallergenic dermatologically tested adhesive 17. Concentric with an outer circumference 18 and exposing a surrounding adhesive layer 19, the heating element 3 is connected by gluing with the adhesive 17 to the base layer 16 facing the area of use, e.g. a body zone 20. In order to avoid direct skin contact in the direction of the body zone 20, the heating element 3 is covered by a resilient self-adhesive cover layer 21, which is microporous in form and thus ensures a breathing activity.

The heating element 3 located between the base layer 16 and the cover layer 21 consists in the embodiment shown of a combination of a surface heating element 22 facing the body zone 20 and a switch element 24, e.g. a transistor, located on an inner surface 23 facing away from the body zone 20 on the surface heating element 22, and forming a spot heat source. The surface heating element 22 consists of a glassfibre-reinforced epoxy resin film 25, upon which is applied a heating conductor layer 26, e.g. by means of a rolled copper layer, which is electrically conductively connected to output 27 of the switching element 24. In order to provide protection against corrosion, the heating conductor layer 26 can be sealed with a protective lacquer layer 23. The cable 4 is connected for power supply to input 29 of the switch element 24.

Before use of the heat transfer element 2 and application of the same on a body zone 20, there is preferably to be provided on the heat transfer element 2, on a surface 30 facing the area of use, a removable hygienic layer consisting e.g. of a transparent plastic film 31, which is to be removed before the heat transfer element 2 is used. After removal of this plastic film 31 from a surrounding adhesive surface 32, the adhesive layer 19 roughly circularly surrounding the heating element 3 is exposed, by means of which the heat transfer element 2 is attached to the body zone 20 provided for treatment.

If the heat transfer element 2 is now connected via the cable 4 to the supply apparatus 5, starting is effected by actuating the on and off switch 10, and the function can be monitored via the monitor lamps 11. These monitor lamps 11 are formed e.g. by LEDs, which display the current flow to the heating element 3 and if necessary the charging condition of the accumulators 7.

As may be better seen in FIG. 1, the control and/or switching device 9 comprises a microprocessor 33 for generating pulse signals for acting on the switch member 24 and for regulating the power flow, so that on the one hand energy-saving operation and on the other hand a heating temperature with minimum temperature tolerances are achieved. Frequently provided further is a multiple-contact switching system 34 for achieving different temperature levels and if necessary a time switch device 35 for pre-selecting a required treatment time and if necessary also a temperature sensor 36 located in the area of the heating element 3 and conductively connected to the control and/or switching device 9 for monitoring the treatment temperature.

As may now be seen from FIG. 2, for use or treatment of a treatment zone the heat transfer element is applied to the body zone 20 via the action of the adhesive layer 19, and the cable 4 is connected to the supply apparatus 5. After the energy supply of the heating element 3 has been set in operation, there is a spot heating of the treatment zone by the switch element 24 until a temperature of about 40° is achieved at that point. During the temperature rise, however, there is a continuous through connection of the switch element 24, so that energy is supplied to the heating conductor layer 26, which is applied on the epoxy resin film 25, and thus the heated area is expanded to the surface area of the epoxy resin film 25 in contact with the heating conductor layer 26. Due to the temperature-dependent energy through-flow, the switch element 24 brings about self-regulation, so that the narrowest temperature tolerances are achieved and heat irritations of the skin are effectively avoided.

In addition to the preferred design described, in which the heat transfer element 2 is rendered self-adhesive by means of the provision of the adhesive layer 19, it is also possible to design it without the adhesive layer 19, in order to avoid negative effects due to chemical impairment of particularly sensitive areas. Thus the heat transfer element 2 may be applied e.g. by means of a pressure bandage, medical adhesive strips, etc., to the body zones 20 to be treater.

A construction is also imaginable in which the heat transfer element 2 has only the surface heating element 22 and the switching element 24, e.g. transistor, FET, etc., necessary for controlling the heating conductor layer 26, is integrated in the control and/or switching device 9. Thus also in particularly tricky cases, a spot heat effect can be avoided.

FIG. 3 shows a further construction of the heating device 1 according to the invention, particularly the heat transfer element 2 in elevation on the surface 30 facing a treatment zone. The heating element 3, as already described in the preceding Figures, is embedded in the base layer 16, forming the upper surface 30, and on the base layer 16 there is applied the cover layer 21, this latter extending concentrically to the circumference 18 of the base layer 16 with an external contour line 37, and exposing the surrounding adhesive surface 32. A non-woven fabric 39 storing therapeutic active ingredients is located in a recess 38 in the cover layer 21. An external contour 40 in this case roughly corresponds to a contour 41 of the heating element 3.

Thus it is possible to reinforce the heat therapy in addition by means of active ingredients, e.g. those obtained from plants or also from chemical processes, and thus to undertake a so-called moist treatment method instead of a dry heat treatment, which brings rapid healing effects due to perfect absorption of the active ingredients through the skin of the treatment zone. Active ingredients for this moist treatment are widely known and available. The described construction of the heating device 1 according to the invention with the heat transfer element 2 ensures a secure seat on the point of treatment, even in the case of movements of the body zone 20, so that heat irritations or changing perception of heat is avoided. In addition to the treatment of disturbances in specific body zones, use of the heating device 1 may also be provided in the area of openings in body zones 20 undertaken for medical intervention in order to maintain the necessary temperature in these areas.

Figure 4:
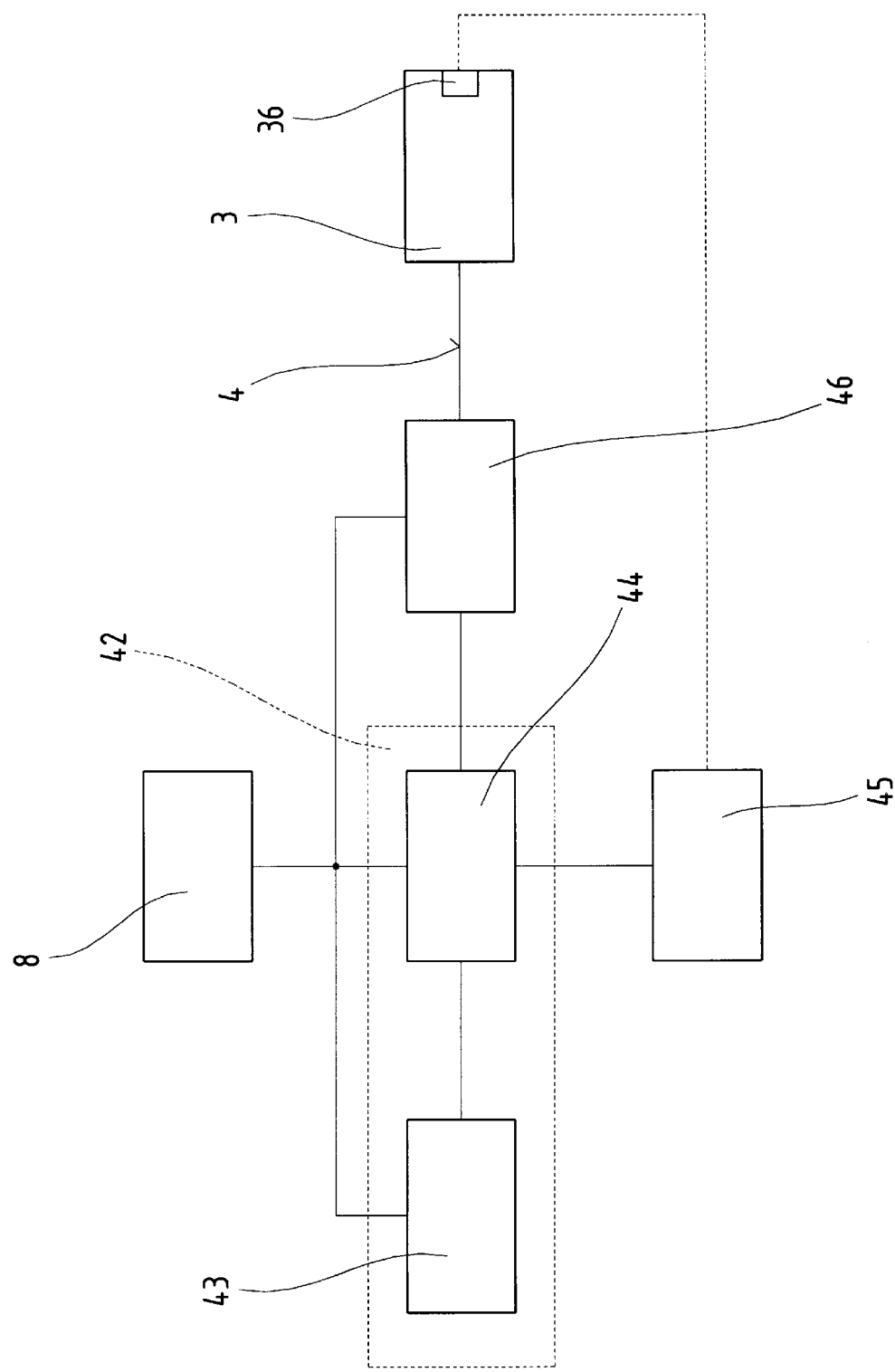
FIG. 4: a circuit diagram of the control and/or switch device of the heating device according to the invention.

FIG. 4 explains with reference to the circuit diagram the function for applying energy to the heating element 3 from the energy source 8, e.g. a nickel cadmium battery. This supply is effected according to the invention via a pulse control module 42 which, substantially comprising an oscillating switching circuit 43 for generating a constant-frequency pulse signal and a pulse modulation switching circuit 44, in dependence on a predetermined required value for the temperature of the heating element 3, emits a pulse width modulated signal to a power end stage 46 by means of a temperature selection regulator 45, e.g. a multiple contact switch. In the power end stage 46, in accordance with the pulse signals, the energy is supplied to the heating element 3 via the cable 4. The heating element 3 is preferably fitted with a temperature sensor 36 for monitoring the temperature of the heating element 3. This latter, as shown in dotted lines, can be connected to the temperature selector regulator 45 so that a corresponding signal for the pulse modulation switching circuit 44 is generated in the temperature selector regulator. By means of such a supply system for the heating element 3 with the necessary energy, on the one hand highly precise regulation is achieved by means of which unpleasant temperature fluctuations are eliminated, and on the other hand an economic utilisation of energy is achieved. This also permits the use of extremely small, easily-handled accumulators, so that the heating device 1 may also be used without difficulty in a mobile manner.

FIG. 5 shows another design of the heating device 1 with a plurality of heat transfer elements 2, e.g. design for glove heating and correspondingly inserted into a glove 47. In this case, from the plug 15 for connection to the supply apparatus 5 a cable cord 48 is provided, which is for example formed by a highly flexible flat cable which, after a branch, forms supply cables 49 for each one of the in all five heat transfer elements 2.

The heat transfer elements 2 consist of an electrical resistive element 50, which is connected to the supply cable 49 and for its protection is glued, welded, etc., in films 51, and has a surface area which roughly corresponds to the magnitude of a fingertip.

The heat transfer elements 2 are preferably fixed in a glove 47 between an outer envelope 52 and an inner liner 53 associated with the fingertips, e.g. by sewing, gluing, etc. The supply cable 49 and also the cable cord 48 are likewise passed between the envelope 52 and the inner liner 53 as far as the area of the terminal collar 54 of the glove 47 and at that point emerges into the open and passes to the final plug 15.

Another design of the heat transfer element 2 of a heating device 1 according to the invention is shown in FIG. 6. In this case the heat transfer element 2 consists of a plate 55, made e.g. of mylar or similar materials, upon which a resistive conductive track 56 is applied, e.g. by powder coating, plasma injection, etc., and which is provided by the plug 15, proceeding from the supply cable 49, with electrical power. The plate 55 with the resistive conductor track 56 is preferably welded in films 51 provided in both sides. At a connection area 57 the supply cables 49 are electrically conductively connected to the resistive conductor track 56, e.g. by soldering. Further, a so-called strain-relief device is provided, the supply cable 49 being connected immobile to the plate 55, e.g. glued in place. The heat transfer element 2, consisting of the film 52 and the plate 55 provided with the resistive conductive track 56, and the supply cables 49 formed as flat conductive cables, have in all a thickness in a range of about 10 mm and is highly flexible in design.

Thus the heat transfer element 2 is particularly suitable for use in the most varied points of the body but also in parts of garments and in this case particularly as a foot heating in shoes, such for example as shoes for winter sport, skiing, etc. For this purpose for example the heating element 2 is incorporated in the material of so-called inner shoes, and used at particularly sensitive areas of the foot, e.g. the ball of the front of the foot, the ball of the heel, etc. Impairment in the wearing comfort of shoes so fitted does not occur. Use of the heating device according to the invention is also possible at any subsequent time for such garments.

FIG. 7 shows another design of the heating device 1. In this, the heat transfer element 2 is strip-shaped and consists of a carrier strip 59, which has for example at opposite end areas 60, 61 and opposed surfaces a VELCRO closure 62. The heating element 3 is located in a central area 63 on the carrier strip 59, covered by the film 51. As already described above, the heating element 3 is for example formed by the plate 55 and the resistive conductor track 56. The supply apparatus 5 is secured on a surface 64 on the carrier strip 59 opposite the heating element. The resistive conductor track 56 is supplied with power from the supply apparatus 5 or the energy source 8 located therein and the control and switching device 9 via the supply cables 49.

Such a design enables the device to be worn in the manner of an armband 65, e.g. in the wrist area of a hand 66. In this way Raynaud's disease can be effectively counteracted, in that due to an expansion of the veins in this area due to heating, a higher blood circulation is enabled, which in turn leads to warming of the hands.

It should be noted that for purposes of comprehensibility of illustration, the individual elements of the heating device 1 in the Figures have been shown out of scale.

What is claimed is:

1. Heating device for heating or maintaining the temperature of a skin surface with a deep effect on a body zone of a human body, comprising:
   a heat transfer element;
   an energy supply device connected via an energy transfer device to the heat transfer element; and
   a control and switching device for controlling a power end stage so as to control energy supply to the heating element from the energy supply device, the control and switching device having an oscillating switching circuit for generating constant pulse signals, and an adjustable pulse modulation switching circuit for altering the pulse signals for controlling the power end stage;
   wherein the heat transfer element comprises a multilayered construction having a film-like base layer formed of a resilient and heat-insulating breathable material, and a heating element attached via an adhesive to an inner side of the base layer, the heating element including a fiber-reinforced resin film attached to the base layer, a heating conductor layer attached to the fiber-reinforced resin film, and a resilient microporous cover layer adhered to and covering the heating conductor layer.

2. Heating device according to claim 1, characterised in that the power end stage is formed by at least one switch member.

3. Heating device according to claim 1, characterised in that the power end stage is located in the energy supply device.

4. Heating device according to claim 1, characterised in that the power end stage is located in the heat transfer element.

5. Heating device according to claim 1, characterised in that the pulse modulation switching circuit is conductively connected to a temperature selector regulator for temperature regulation of the heating element.

6. Heating device according to claim 1, characterised in that the heating device includes an adhesive layer disposed so as to contact and attach the heating device to the body zone.

7. Heating device according to claim 1, characterised in that the heating element includes a semi-conductor component forming a spot heat source connected to the heating conductor layer.

8. Heating device according to claim 1, characterised in that the cover layer is located on a heat transfer surface of the heating element that faces toward the skin surface and away from the inner side.

9. Heating device according to claim 1, characterised in that the heating device includes an adhesive layer located on at least one of a support surface of the base layer facing the body zone and a base surface of the cover layer facing the body zone, said adhesive layer being adapted to attach the heating device to the skin surface.

10. Heating device according to claim 9, characterised in that an adhesive surface of the adhesive layer has a configuration annularly surrounding the cover layer.

11. Heating device according to claim 9, characterised in that the heat transfer element, for protection from contamination during transport and storage, is provided on a contact surface having the adhesive surface with a detachable plastic film.

12. Heating device according to claim 1, characterised in that the base layer forms a recess in which the heating element is located.

13. Heating device according to claim 1, characterised in that the base layer of the heating element is formed from a glass fiber-reinforced epoxy resin film.

14. Heating device according to claim 1, characterised in that the heating conductive layer is formed of at least one of rolled copper, silver, and oxides thereof.

15. Heating device according to claim 1, characterised in that the cover layer is formed from resilient non-woven material with a hypoallergenic adhesive.

16. Heating device according to claim 1, characterised in that the base layer has an aperture which surrounds a cable of the energy transfer device.

17. Heating device according to claim 16, characterised in that the cable has a plug for detachable connection to the energy supply device.

18. Heating device according to claim 1, characterised in that the cover layer has a recess in a side thereof that faces the skin surface, and a non-woven material is disposed in the recess.

19. Heating device according to claim 18, characterised in that the non-woven material serves to accommodate a liquid active ingredient.

20. Heating device according to claim 1, characterised in that the energy supply device comprises a portable supply apparatus provided with chargeable accumulators, is conductively connected to the heating element for energy supply thereof.

21. Heating device according to claim 1, characterised in that the control and switching device is located in the energy supply device.

22. Heating device according to claim 1, characterised in that a plurality of heat transfer elements are connected to a supply apparatus via a supply cable.

23. Heating device according to claim 1, characterised in that at least one heat transfer element is located in a glove.

24. Heating device according to claim 1, characterised in that at least one heat transfer element is located in a shoe.

25. Heating device according to claim 1, characterised in that the heat transfer element is attached to a carrier strip.

26. Heating device according to claim 25, characterised in that end portions of the carrier strip have hook and loop fasteners.

* * * * *